Figure 1A:
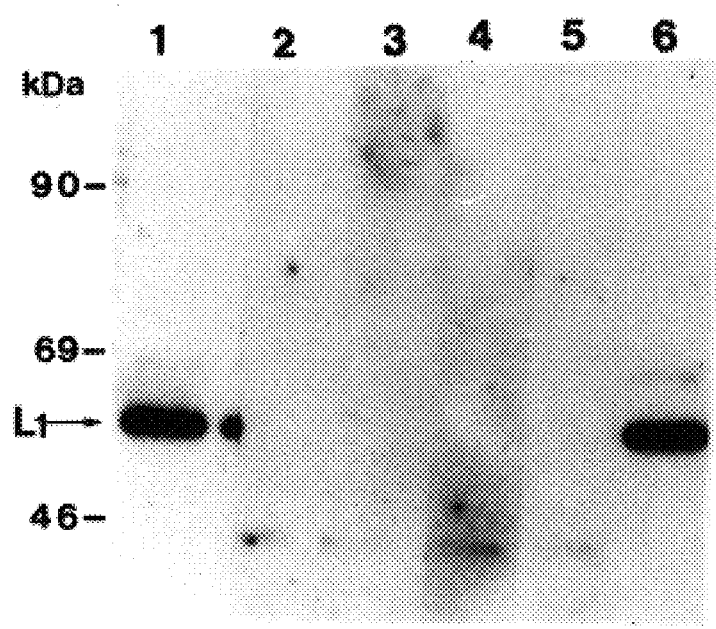

United States Patent [19]

Frazer et al.

[11] Patent Number: 5,993,821

[45] Date of Patent: *Nov. 30, 1999

[54] MODIFIED PAPILLOMA VIRUS L2 PROTEIN AND VLPS FORMED THEREFROM

[75] Inventors: Ian Frazer, St. Lucia; Jian Zhou, Jindalee, both of Australia

[73] Assignees: The University of Queensland, Queensland; CSL Limited, Victoria, both of Australia

[ * ] Notice: This patent issued on a continued prosecution application filed under 37 CFR 1.53(d), and is subject to the twenty year patent term provisions of 35 U.S.C. 154(a)(2).

[21] Appl. No.: 08/700,670

[22] Filed: Jul. 30, 1996

Related U.S. Application Data

[63] Continuation of application No. PCT/AU95/00043, Jan. 31, 1995.

[30] Foreign Application Priority Data

Jan. 31, 1994 [AU] Australia .................................. PM3588

[51] Int. Cl.⁶ .............................. A61K 39/12; C12N 7/00; C12N 7/01

[52] U.S. Cl. ...................................... 424/204.1; 424/199.1; 435/69.1; 435/69.3; 435/235.1; 435/440; 536/23.72; 935/65

[58] Field of Search ............................... 424/199.1, 204.1; 435/69.1, 69.3, 440, 235.1; 536/23.72; 935/65

[56] References Cited

FOREIGN PATENT DOCUMENTS

| WO 93/00436 | 1/1993 | WIPO . |
| WO 93/02184 | 2/1993 | WIPO . |
| WO 94/20137 | 9/1994 | WIPO . |
| WO 94/23037 | 10/1994 | WIPO . |

*Primary Examiner*—Mary E. Mosher
*Assistant Examiner*—Ali R Salimi
*Attorney, Agent, or Firm*—Foley & Lardner

[57] ABSTRACT

The invention, in one aspect, is directed to a modified papilloma virus L2 protein which does not bind DNA or which has a substantially impaired ability to bind DNA compared to wild-type papilloma virus L2 protein. The invention is also directed to a method of producing one or more virus-like particles comprising a modified papilloma virus L2 protein according to the invention. The invention also resides in virus-like particles produced from this method.

23 Claims, 8 Drawing Sheets

| | | DNA binding |
|---|---|:---:|
| HPV16L2 | MRHKRSAKRTKRASATQLYKTCKQAGTCPP | + |
| Δ2 | ------------------------------ | − |
| Δ15 |                --------------- | − |
| R2P | -P---------------------------- | − |
| H3P | --P--------------------------- | + |
| K4P | ---P-------------------------- | − |
| 2,4,5N | -N-NN------------------------- | − |
| R5P | ----P------------------------- | + |
| S6N | -----N------------------------ | − |
| S6P | -----P------------------------ | + |
| A7P | ------P----------------------- | + |
| K8P | -------P---------------------- | − |
| R9P | --------P--------------------- | + |
| 8,9N | -------NN--------------------- | − |
| 6,10N | -----N---N-------------------- | − |
| 11,12N | ----------NN------------------ | − |
| 6,10,14N | -----N---N---N---------------- | − |

FIG. 4

```
  1 Met Arg His Lys Arg Ser Ala Lys Arg Thr Lys Arg Ala Ser Ala  15
 16 Thr Gln Leu Tyr Lys Thr Cys Lys Gln Ala Gly Thr Cys Pro Pro  30
 31 Asp Ile Ile Pro Lys Val Glu Gly Lys Thr Ile Ala Glu Gln Ile  45
 46 Leu Gln Tyr Gly Ser Met Gly Val Phe Phe Gly Gly Leu Gly Ile  60
 61 Gly Thr Gly Ser Gly Thr Gly Gly Arg Thr Gly Tyr Ile Pro Leu  75

76 Gly Thr Arg Pro Pro Thr Ala Thr Asp Thr Leu Ala Pro Val Arg  90
 91 Pro Pro Leu Thr Val Asp Pro Val Gly Pro Ser Asp Pro Ser Ile 105
106 Val Ser Leu Val Glu Glu Thr Ser Phe Ile Asp Ala Gly Ala Pro 120
121 Thr Ser Val Pro Ser Ile Pro Pro Asp Val Ser Gly Phe Ser Ile 135
136 Thr Thr Ser Thr Asp Thr Thr Pro Ala Ile Leu Asp Ile Asn Asn 150

151 Thr Val Thr Thr Val Thr Thr His Asn Asn Pro Thr Phe Thr Asp 165
166 Pro Ser Val Leu Gln Pro Pro Thr Pro Ala Glu Thr Gly Gly His 180
181 Phe Thr Leu Ser Ser Ser Thr Ile Ser Thr His Asn Tyr Glu Glu 195
196 Ile Pro Met Asp Thr Phe Ile Val Ser Thr Asn Pro Asn Thr Val 210
211 Thr Ser Ser Thr Pro Ile Pro Gly Ser Arg Pro Val Ala Arg Leu 225

226 Gly Leu Tyr Ser Arg Thr Thr Gln Gln Val Lys Val Val Asp Pro 240
241 Ala Phe Val Thr Thr Pro Thr Lys Leu Ile Thr Tyr Asp Asn Pro 255
256 Ala Tyr Glu Gly Ile Asp Val Asp Asn Thr Leu Tyr Phe Ser Ser 270
271 Asn Asp Asn Ser Ile Asn Ile Ala Pro Asp Pro Asp Phe Leu Asp 285
286 Ile Val Ala Leu His Arg Pro Ala Leu Thr Ser Arg Arg Thr Gly 300

301 Ile Arg Tyr Ser Arg Ile Gly Asn Lys Gln Thr Leu Arg Thr Arg 315
316 Ser Gly Lys Ser Ile Gly Ala Lys Val His Tyr Tyr Tyr Asp Leu 330
331 Ser Thr Ile Asp Pro Ala Glu Glu Ile Glu Leu Gln Thr Ile Thr 345
346 Pro Ser Thr Tyr Thr Thr Thr Ser His Ala Ala Ser Pro Thr Ser 360
361 Ile Asn Asn Gly Leu Tyr Asp Ile Tyr Ala Asp Asp Phe Ile Thr 375

376 Asp Thr Ser Thr Thr Pro Val Pro Ser Val Pro Ser Thr Ser Leu 390
391 Ser Gly Tyr Ile Pro Ala Asn Thr Thr Ile Pro Phe Gly Gly Ala 405
406 Tyr Asn Ile Pro Leu Val Ser Gly Pro Asp Ile Pro Ile Asn Ile 420
421 Thr Asp Gln Ala Pro Ser Leu Ile Pro Ile Val Pro Gly Ser Pro 435
436 Gln Tyr Thr Ile Ile Ala Asp Ala Gly Asp Phe Tyr Leu His Pro 450

451 Ser Tyr Tyr Met Leu Arg Lys Arg Arg Lys Arg Leu Pro Tyr Phe 465
466 Phe Ser Asp Val Ser Leu Ala Ala Ter                         474
```

FIG. 6

```
   1 ATGCGACACAAACGTTCTGCAAAACGCACAAACGTGCATCGGCTACCCAACTTTATAAA    60
  61 ACATGCAAACAGGCAGGTACACCTGTCCACCTGACATTATACCTAAGGTTGAAGGCAAACT   120
 121 ATTGCTGAACAAATATTACAATATGGAACTATGGGTGTATTTTTGGTGGGTTAGGAATT    180
 181 GGAACAGGGTCGGGTACACAGGCGGACGCACTGGGTATATTCCATTGGGAACAAGGCCTCCC   240
 241 ACAGCTACAGATACACCTTGCTCCTGTAAGACCCCTTTAACAGTAGATCCTGTGGGCCCT    300
 301 TCTGATCCTTCTATAGTTTCTTTAGTGGAAGAAACTAGTTTTATTGATGCTGGTGCACCA    360
 361 ACATCTGTACCTTCCATTCCCCCAGATGTATCAGGATTTAGTATTACTACTTCAACTGAT    420
 421 ACCACACCTGCTATATTAGATATTAATAATACTGTTACTACTGTTACTACACATAATAAT    480
 481 CCCACTTTCACTGACCATCTGTATTGCAGCCTCCAACACCTGCAGAAACTGGAGGGCAT    540
 541 TTTACACTTTCATCATCCACTATTAGTACACATAATTATGAAGAAATTCCTATGGATACA    600
 601 TTTATTGTTAGCACAAACCCTAACACAGTAACTAGTAGCACACCCATACCAGGGTCTCGC    660
 661 CCAGTGGCACGCCTAGGATTATATAGTCGCACACAACAGTTAAGTTGTAGACCCT        720
 721 GCTTTTGTAACCACTCCCACTAACTTATTACATATGATAATCCTGCATATGAAGGTATA    780
 781 GATGTGGATAATACATTATATTTTCTAGTAATGATAATAGTATTAATATAGCTCCAGAT    840
 841 CCTGACTTTTTGGATATAGTTGCTTTACATAGTGCATTAACCCTCTAGGCGTACTGGC    900
 901 ATTAGGTACAGTAGAATTGGTAATAAACAAACACTACGTACTCGTAGTGGAAAATCTATA    960
 961 GGTGCTAAGGTACATTATTATTGATTAAGTACTATTGATCCTGCAGAAGAAATAGAA    1020
1021 TTACAAACTATAACACCTTCTACATATATTTATGCAGATGACTTTATTACAGATACTTCT    1080
1081 ATTAATAATGGATTATATGCCTCTACATCTTTATCAGGTTATATTCCTGCAAATACAACAATT    1140
1141 CCGGTACCATCTGTACCCTCTACACTCTTTATCAGGTTATATTCCTGCAAATACAACAATT    1200
1201 CCTTTTGGTGGTGCATACAATATTCCTTTAGTATCAGGTCCTGATATACCCATTAATATA    1260
1261 ACTGACCAAGCTCCTTCATTAATTCCTATAGTTCCAGGGTCTCCACAATATACAATTATT    1320
1321 GCTGATGCCAGGTGACTTTTATTACATCCTAGTTATTACATGTTACGAAAAACGACGTAAA    1380
1381 CGTTTACCATATTTTTTTCAGATGTCTCTTTGGCTGCCTAG                      1422
```

FIG. 7

C-TERMINAL DELETIONS

5' COMMON PRIMER:
M13RSP:    5'CAGGAAACAGCTATGAC

3' PRIMERS
Δ374:    5'CGCCCGGGTTAAAAGTCATCTGCATAAATATCATATAATCC
Δ384:    5'CGCCCGGGTTATGGTACCGGGGTTGTAGAAGTATCTGTAATAAAG
Δ394:    5'CGCCCGGGTTAATAACCTGATAAAGATGTAGAGGGTACAGATGG
Δ404:    5'CGCCCGGGTTAACCAAAAGGAATTGTTGTATTTGCAGGAATATAACC
Δ414:    5'CGCCCGGGTTAACCTGATACTAAAGGAATATTGTATGCACC

N-TERMINAL MUTATIONS

5' PRIMERS FOR DELETION MUTATION:
Δ1-2:    5'GCGGATCCATGCACAAACGTTCTGCAAAACGC
Δ1-3:    5'GCGGATCCATGAAACGTTCTGCAAAACGCACAAAACG
Δ1-4:    5'GCGGATCCATGCGTTCTGCAAAACGCACAAAACGTGC
Δ1-5:    5'GCGGATCCATGTCTGCAAAACGCACAAAACGTGCATCGG
Δ1-6:    5'GCGGATCCATGGCAAAACGCACAAAACGTGCATCGGC
Δ1-7:    5'GCGGATCCATGAAACGCACAAAACGTGCATCGGCTACC
Δ1-8:    5'GCGGATCCATGCGCACAAAACGTGCATCGGCTACCC
Δ1-9:    5'GCGGATCCATGACAAAACGTGCATCGGCTACCCAAC
Δ1-10:   5'GCGGATCCATGAAACGTGCATCGGCTACCCAACTTTATAAAAC
Δ1-11:   5'GCGGATCCATGCGTGCATCGGCTACCCAACTTTATAAAAC
Δ1-12:   5'GCGGATCCATGGCATCGGCTACCCAACTTTATAAAAC
Δ1-13:   5'GCGGATCCATGTCGGCTACCCAACTTTATAAAACATG
Δ1-14:   5'GCGGATCCATGGCTACCCAACTTTATAAAACATGC
Δ1-15:   5'GCGGATCCATGACCCAACTTTATAAAACATGCAAACAGG
Δ1-20:   5'GCGGATCCATGACATGCAAACAGGCAGGTACATGTCC
Δ1-40:   5'GCGGATCCATGATTGCTGAACAAATATTACAATATGG
Δ1-60:   5'GCGGATCCATGGGAACAGGGTCGGGTACAGGCGGACG
Δ1-80:   5'GCGGATCCATGACAGCTACAGATACACTTGCTCCTG
Δ1-100:  5'GCGGATCCATGTCTGATCCTTCTATAGTTTCTTTAG

5' PRIMERS FOR POINT MUTATIONS:
H3P:     5'GCGGATCCATGCGACCCAAACGTTCTGCAAAACG
K4P:     5'GCGGATCCATGCGACACCCACGTTCTGCAAAACG
2,4,5N:  5'GCGGATCCATGAATCACAATAATTCTGCAAAACGCACAAAACG
R5P:     5'GCGGATCCATGCGACACAAACCTTCTGCAAAACG
S6N:     5'GCGGATCCATGCGACACAAACGTAATGCAAAACGCACAAAACG
S6P:     5'GCGGATCCATGCGACACAAACGTCCTGCAAAACG
A7P:     5'GCGGATCCATGCGACACAAACGTTCTCCAAAACGCAC
K8P:     5'GCGGATCCATGCGACACAAACGTTCTGCACCACGCACAAAACG
R9P:     5'GCGGATCCATGCGACACAAACGTTCTGCAAAACCCACAAAACG
8,9N:    5'CGGGATCCATGCGACACAAACGTTCTGCAAATAACACAAAACGTGC

3' COMMON PRIMER:
L2-END:  5'CGCCCGGGCTAGGCAGCCAAAGAGACATCTGAAAAAAAATATGG

FIG. 8

SEQUENCE LISTING (1) GENERAL INFORMATION:

(iii) NUMBER OF SEQUENCES: 59

(2) INFORMATION FOR SEQ ID NO:1:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (xi) SEQUENCE DESCRIPTION: SEQ ID NO:1:

CAGGTCAGAT CAGCGGATCC TGTCG                                              25

(2) INFORMATION FOR SEQ ID NO:2:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:2:

GAGGCGAATT CAGTGCATGT GCAGC                                              25

(2) INFORMATION FOR SEQ ID NO:3:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:3:

GCTGCACATG CACTGAATTC GCCTC                                              25

(2) INFORMATION FOR SEQ ID NO:4:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:4:

CAGGTCAGAT CAGCGGATCC TGTCG                                              25

(2) INFORMATION FOR SEQ ID NO:5:

(i) SEQUENCE CHARACTERISTICS:
        (A) LENGTH: 30 amino acids
        (B) TYPE: amino acid
        (C) STRANDEDNESS: single
        (D) TOPOLOGY: linear (xi) SEQUENCE DESCRIPTION: SEQ ID NO:5:

Met Arg His Lys Arg Ser Ala Lys Arg Thr Lys Arg Ala Ser Ala Thr
1               5                   10                  15

Gln Leu Tyr Lys Thr Cys Lys Gln Ala Gly Thr Cys Pro Pro
            20                  25                  30

(2) INFORMATION FOR SEQ ID NO:6:

(i) SEQUENCE CHARACTERISTICS:
        (A) LENGTH: 28 amino acids
        (B) TYPE: amino acid
        (C) STRANDEDNESS: single
        (D) TOPOLOGY: linear (xi) SEQUENCE DESCRIPTION: SEQ ID NO:6:

His Lys Arg Ser Ala Lys Arg Thr Lys Arg Ala Ser Ala Thr Gln Leu
1               5                   10                  15

Tyr Lys Thr Cys Lys Gln Ala Gly Thr Cys Pro Pro
            20                  25

(2) INFORMATION FOR SEQ ID NO:7:

(i) SEQUENCE CHARACTERISTICS:
        (A) LENGTH: 15 amino acids
        (B) TYPE: amino acid
        (C) STRANDEDNESS: single
        (D) TOPOLOGY: linear (xi) SEQUENCE DESCRIPTION: SEQ ID NO:7:

Thr Gln Leu Tyr Lys Thr Cys Lys Gln Ala Gly Thr Cys Pro Pro
1               5                  10                  15

(2) INFORMATION FOR SEQ ID NO:8:

(i) SEQUENCE CHARACTERISTICS:
        (A) LENGTH: 30 amino acids
        (B) TYPE: amino acid
        (C) STRANDEDNESS: single
        (D) TOPOLOGY: linear (xi) SEQUENCE DESCRIPTION: SEQ ID NO:8:

Met Pro His Lys Arg Ser Ala Lys Arg Thr Lys Arg Ala Ser Ala Thr
1               5                  10                  15

Gln Leu Tyr Lys Thr Cys Lys Gln Ala Gly Thr Cys Pro Pro
            20                  25                  30

(2) INFORMATION FOR SEQ ID NO:9:

(i) SEQUENCE CHARACTERISTICS:
        (A) LENGTH: 30 amino acids
        (B) TYPE: amino acid
        (C) STRANDEDNESS: single
        (D) TOPOLOGY: linear (xi) SEQUENCE DESCRIPTION: SEQ ID NO:9:

Met Arg Pro Lys Arg Ser Ala Lys Arg Thr Lys Arg Ala Ser Ala Thr
1               5                  10                  15

Gln Leu Tyr Lys Thr Cys Lys Gln Ala Gly Thr Cys Pro Pro
            20                  25                  30

(2) INFORMATION FOR SEQ ID NO:10:

(i) SEQUENCE CHARACTERISTICS:
        (A) LENGTH: 30 amino acids
        (B) TYPE: amino acid
        (C) STRANDEDNESS: single
        (D) TOPOLOGY: linear (xi) SEQUENCE DESCRIPTION: SEQ ID NO:10:

Met Arg His Pro Arg Ser Ala Lys Arg Thr Lys Arg Ala Ser Ala Thr
1               5                  10                  15

Gln Leu Tyr Lys Thr Cys Lys Gln Ala Gly Thr Cys Pro Pro
            20                  25                  30

(2) INFORMATION FOR SEQ ID NO:11:

(i) SEQUENCE CHARACTERISTICS:
        (A) LENGTH: 30 amino acids
        (B) TYPE: amino acid
        (C) STRANDEDNESS: single
        (D) TOPOLOGY: linear (xi) SEQUENCE DESCRIPTION: SEQ ID NO:11:

Met Asn His Asn Asn Ser Ala Lys Arg Thr Lys Arg Ala Ser Ala Thr
1               5                  10                  15

Gln Leu Tyr Lys Thr Cys Lys Gln Ala Gly Thr Cys Pro Pro
            20                  25                  30

(2) INFORMATION FOR SEQ ID NO:12:

(i) SEQUENCE CHARACTERISTICS:
        (A) LENGTH: 30 amino acids
        (B) TYPE: amino acid
        (C) STRANDEDNESS: single
        (D) TOPOLOGY: linear (xi) SEQUENCE DESCRIPTION: SEQ ID NO:12:

```
Met Arg His Lys Pro Ser Ala Lys Arg Thr Lys Arg Ala Ser Ala Thr
1               5                   10                  15

Gln Leu Tyr Lys Thr Cys Lys Gln Ala Gly Thr Cys Pro Pro
            20                  25                  30
```

(2) INFORMATION FOR SEQ ID NO:13:

(i) SEQUENCE CHARACTERISTICS:
        (A) LENGTH: 30 amino acids
        (B) TYPE: amino acid
        (C) STRANDEDNESS: single
        (D) TOPOLOGY: linear (xi) SEQUENCE DESCRIPTION: SEQ ID NO:13:

```
Met Arg His Lys Arg Asn Ala Lys Arg Thr Lys Arg Ala Ser Ala Thr
1               5                   10                  15

Gln Leu Tyr Lys Thr Cys Lys Gln Ala Gly Thr Cys Pro Pro
            20                  25                  30
```

(2) INFORMATION FOR SEQ ID NO:14:

(i) SEQUENCE CHARACTERISTICS:
        (A) LENGTH: 30 amino acids
        (B) TYPE: amino acid
        (C) STRANDEDNESS: single
        (D) TOPOLOGY: linear (xi) SEQUENCE DESCRIPTION: SEQ ID NO:14:

```
Met Arg His Lys Arg Pro Ala Lys Arg Thr Lys Arg Ala Ser Ala Thr
1               5                   10                  15

Gln Leu Tyr Lys Thr Cys Lys Gln Ala Gly Thr Cys Pro Pro
            20                  25                  30
```

(2) INFORMATION FOR SEQ ID NO:15:

(i) SEQUENCE CHARACTERISTICS:
        (A) LENGTH: 30 amino acids
        (B) TYPE: amino acid
        (C) STRANDEDNESS: single
        (D) TOPOLOGY: linear (xi) SEQUENCE DESCRIPTION: SEQ ID NO:15:

```
Met Arg His Lys Arg Ser Pro Lys Arg Thr Lys Arg Ala Ser Ala Thr
1               5                   10                  15

Gln Leu Tyr Lys Thr Cys Lys Gln Ala Gly Thr Cys Pro Pro
            20                  25                  30
```

(2) INFORMATION FOR SEQ ID NO:16:

(i) SEQUENCE CHARACTERISTICS:
        (A) LENGTH: 30 amino acids
        (B) TYPE: amino acid
        (C) STRANDEDNESS: single
        (D) TOPOLOGY: linear (xi) SEQUENCE DESCRIPTION: SEQ ID NO:16:

```
Met Arg His Lys Arg Ser Ala Pro Arg Thr Lys Arg Ala Ser Ala Thr
1               5                   10                  15
```

```
Gln Leu Tyr Lys Thr Cys Lys Gln Ala Gly Thr Cys Pro Pro
            20                  25                  30
```

(2) INFORMATION FOR SEQ ID NO:17:

(i) SEQUENCE CHARACTERISTICS:
        (A) LENGTH: 30 amino acids
        (B) TYPE: amino acid
        (C) STRANDEDNESS: single
        (D) TOPOLOGY: linear (xi) SEQUENCE DESCRIPTION: SEQ ID NO:17:

```
Met Arg His Lys Arg Ser Ala Lys Pro Thr Lys Arg Ala Ser Ala Thr
 1               5                  10                  15
Gln Leu Tyr Lys Thr Cys Lys Gln Ala Gly Thr Cys Pro Pro
            20                  25                  30
```

(2) INFORMATION FOR SEQ ID NO:18:

(i) SEQUENCE CHARACTERISTICS:
        (A) LENGTH: 30 amino acids
        (B) TYPE: amino acid
        (C) STRANDEDNESS: single
        (D) TOPOLOGY: linear (xi) SEQUENCE DESCRIPTION: SEQ ID NO:18:

```
Met Arg His Lys Arg Ser Ala Asn Asn Thr Lys Arg Ala Ser Ala Thr
 1               5                  10                  15
Gln Leu Tyr Lys Thr Cys Lys Gln Ala Gly Thr Cys Pro Pro
            20                  25                  30
```

(2) INFORMATION FOR SEQ ID NO:19:

(i) SEQUENCE CHARACTERISTICS:
        (A) LENGTH: 30 amino acids
        (B) TYPE: amino acid
        (C) STRANDEDNESS: single
        (D) TOPOLOGY: linear (xi) SEQUENCE DESCRIPTION: SEQ ID NO:19:

```
Met Arg His Lys Arg Asn Ala Lys Arg Asn Lys Arg Ala Ser Ala Thr
 1               5                  10                  15
Gln Leu Tyr Lys Thr Cys Lys Gln Ala Gly Thr Cys Pro Pro
            20                  25                  30
```

(2) INFORMATION FOR SEQ ID NO:20:

(i) SEQUENCE CHARACTERISTICS:
        (A) LENGTH: 30 amino acids
        (B) TYPE: amino acid
        (C) STRANDEDNESS: single
        (D) TOPOLOGY: linear (xi) SEQUENCE DESCRIPTION: SEQ ID NO:20:

```
Met Arg His Lys Arg Ser Ala Lys Arg Thr Asn Asn Ala Ser Ala Thr
 1               5                  10                  15
Gln Leu Tyr Lys Thr Cys Lys Gln Ala Gly Thr Cys Pro Pro
            20                  25                  30
```

(2) INFORMATION FOR SEQ ID NO:21:

(i) SEQUENCE CHARACTERISTICS:
        (A) LENGTH: 30 amino acids
        (B) TYPE: amino acid
        (C) STRANDEDNESS: single
        (D) TOPOLOGY: linear (xi) SEQUENCE DESCRIPTION: SEQ ID NO:21:

Met Arg His Lys Arg Asn Ala Lys Arg Asn Lys Arg Ala Asn Ala Thr
1               5                   10                  15

Gln Leu Tyr Lys Thr Cys Lys Gln Ala Gly Thr Cys Pro Pro
            20                  25                  30

(2) INFORMATION FOR SEQ ID NO:22:

(i) SEQUENCE CHARACTERISTICS:
        (A) LENGTH: 1422 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1419

(xi) SEQUENCE DESCRIPTION: SEQ ID NO:22:

```
ATG CGA CAC AAA CGT TCT GCA AAA CGC ACA AAA CGT GCA TCG GCT ACC        48
Met Arg His Lys Arg Ser Ala Lys Arg Thr Lys Arg Ala Ser Ala Thr
1               5                   10                  15

CAA CTT TAT AAA ACA TGC AAA CAG GCA GGT ACA TGT CCA CCT GAC ATT        96
Gln Leu Tyr Lys Thr Cys Lys Gln Ala Gly Thr Cys Pro Pro Asp Ile
            20                  25                  30

ATA CCT AAG GTT GAA GGC AAA ACT ATT GCT GAA CAA ATA TTA CAA TAT       144
Ile Pro Lys Val Glu Gly Lys Thr Ile Ala Glu Gln Ile Leu Gln Tyr
        35                  40                  45

GGA ACT ATG GGT GTA TTT TTT GGT GGG TTA GGA ATT GGA ACA GGG TCG       192
Gly Thr Met Gly Val Phe Phe Gly Gly Leu Gly Ile Gly Thr Gly Ser
    50                  55                  60

GGT ACA GGC GGA CGC ACT GGG TAT ATT CCA TTG GGA ACA AGG CCT CCC       240
Gly Thr Gly Gly Arg Thr Gly Tyr Ile Pro Leu Gly Thr Arg Pro Pro
65                  70                  75                  80

ACA GCT ACA GAT ACA CTT GCT CCT GTA AGA CCC CCT TTA ACA GTA GAT       288
Thr Ala Thr Asp Thr Leu Ala Pro Val Arg Pro Pro Leu Thr Val Asp
                85                  90                  95

CCT GTG GGC CCT TCT GAT CCT TCT ATA GTT TCT TTA GTG GAA GAA ACT       336
Pro Val Gly Pro Ser Asp Pro Ser Ile Val Ser Leu Val Glu Glu Thr
            100                 105                 110

AGT TTT ATT GAT GCT GGT GCA CCA ACA TCT GTA CCT TCC ATT CCC CCA       384
Ser Phe Ile Asp Ala Gly Ala Pro Thr Ser Val Pro Ser Ile Pro Pro
        115                 120                 125

GAT GTA TCA GGA TTT AGT ATT ACT ACT TCA ACT GAT ACC ACA CCT GCT       432
Asp Val Ser Gly Phe Ser Ile Thr Thr Ser Thr Asp Thr Thr Pro Ala
    130                 135                 140

ATA TTA GAT ATT AAT AAT ACT GTT ACT ACT GTT ACT ACA CAT AAT AAT       480
Ile Leu Asp Ile Asn Asn Thr Val Thr Thr Val Thr Thr His Asn Asn
145                 150                 155                 160

CCC ACT TTC ACT GAC CCA TCT GTA TTG CAG CCT CCA ACA CCT GCA GAA       528
Pro Thr Phe Thr Asp Pro Ser Val Leu Gln Pro Pro Thr Pro Ala Glu
                165                 170                 175

ACT GGA GGG CAT TTT ACA CTT TCA TCA TCC ACT ATT AGT ACA CAT AAT       576
Thr Gly Gly His Phe Thr Leu Ser Ser Ser Thr Ile Ser Thr His Asn
            180                 185                 190

TAT GAA GAA ATT CCT ATG GAT ACA TTT ATT GTT AGC ACA AAC CCT AAC       624
Tyr Glu Glu Ile Pro Met Asp Thr Phe Ile Val Ser Thr Asn Pro Asn
        195                 200                 205

ACA GTA ACT AGT AGC ACA CCC ATA CCA GGG TCT CGC CCA GTG GCA CGC       672
Thr Val Thr Ser Ser Thr Pro Ile Pro Gly Ser Arg Pro Val Ala Arg
    210                 215                 220
```

-continued

```
CTA GGA TTA TAT AGT CGC ACA ACA CAA CAG GTT AAA GTT GTA GAC CCT                720
Leu Gly Leu Tyr Ser Arg Thr Thr Gln Gln Val Lys Val Val Asp Pro
225                 230                 235                 240

GCT TTT GTA ACC ACT CCC ACT AAA CTT ATT ACA TAT GAT AAT CCT GCA                768
Ala Phe Val Thr Thr Pro Thr Lys Leu Ile Thr Tyr Asp Asn Pro Ala
                245                 250                 255

TAT GAA GGT ATA GAT GTG GAT AAT ACA TTA TAT TTT TCT AGT AAT GAT                816
Tyr Glu Gly Ile Asp Val Asp Asn Thr Leu Tyr Phe Ser Ser Asn Asp
            260                 265                 270

AAT AGT ATT AAT ATA GCT CCA GAT CCT GAC TTT TTG GAT ATA GTT GCT                864
Asn Ser Ile Asn Ile Ala Pro Asp Pro Asp Phe Leu Asp Ile Val Ala
        275                 280                 285

TTA CAT AGG CCA GCA TTA ACC TCT AGG CGT ACT GGC ATT AGG TAC AGT                912
Leu His Arg Pro Ala Leu Thr Ser Arg Arg Thr Gly Ile Arg Tyr Ser
    290                 295                 300

AGA ATT GGT AAT AAA CAA ACA CTA CGT ACT CGT AGT GGA AAA TCT ATA                960
Arg Ile Gly Asn Lys Gln Thr Leu Arg Thr Arg Ser Gly Lys Ser Ile
305                 310                 315                 320

GGT GCT AAG GTA CAT TAT TAT TAT GAT TTA AGT ACT ATT GAT CCT GCA               1008
Gly Ala Lys Val His Tyr Tyr Tyr Asp Leu Ser Thr Ile Asp Pro Ala
                325                 330                 335

GAA GAA ATA GAA TTA CAA ACT ATA ACA CCT TCT ACA TAT ACT ACC ACT               1056
Glu Glu Ile Glu Leu Gln Thr Ile Thr Pro Ser Thr Tyr Thr Thr Thr
                340                 345                 350

TCA CAT GCA GCC TCA CCT ACT TCT ATT AAT AAT GGA TTA TAT GAT ATT               1104
Ser His Ala Ala Ser Pro Thr Ser Ile Asn Asn Gly Leu Tyr Asp Ile
            355                 360                 365

TAT GCA GAT GAC TTT ATT ACA GAT ACT TCT ACA ACC CCG GTA CCA TCT               1152
Tyr Ala Asp Asp Phe Ile Thr Asp Thr Ser Thr Thr Pro Val Pro Ser
        370                 375                 380

GTA CCC TCT ACA TCT TTA TCA GGT TAT ATT CCT GCA AAT ACA ACA ATT               1200
Val Pro Ser Thr Ser Leu Ser Gly Tyr Ile Pro Ala Asn Thr Thr Ile
385                 390                 395                 400

CCT TTT GGT GGT GCA TAC AAT ATT CCT TTA GTA TCA GGT CCT GAT ATA               1248
Pro Phe Gly Gly Ala Tyr Asn Ile Pro Leu Val Ser Gly Pro Asp Ile
                405                 410                 415

CCC ATT AAT ATA ACT GAC CAA GCT CCT TCA TTA ATT CCT ATA GTT CCA               1296
Pro Ile Asn Ile Thr Asp Gln Ala Pro Ser Leu Ile Pro Ile Val Pro
                420                 425                 430

GGG TCT CCA CAA TAT ACA ATT ATT GCT GAT GCA GGT GAC TTT TAT TTA               1344
Gly Ser Pro Gln Tyr Thr Ile Ile Ala Asp Ala Gly Asp Phe Tyr Leu
            435                 440                 445

CAT CCT AGT TAT TAC ATG TTA CGA AAA CGA CGT AAA CGT TTA CCA TAT               1392
His Pro Ser Tyr Tyr Met Leu Arg Lys Arg Arg Lys Arg Leu Pro Tyr
        450                 455                 460

TTT TTT TCA GAT GTC TCT TTG GCT GCC TAG                                       1422
Phe Phe Ser Asp Val Ser Leu Ala Ala
465                 470
```

(2) INFORMATION FOR SEQ ID NO:23:

(i) SEQUENCE CHARACTERISTICS:
        (A) LENGTH: 473 amino acids
        (B) TYPE: amino acid
        (D) TOPOLOGY: linear (ii) MOLECULE TYPE: protein (xi) SEQUENCE DESCRIPTION: SEQ ID NO:23:

```
Met Arg His Lys Arg Ser Ala Lys Arg Thr Lys Arg Ala Ser Ala Thr
1               5                   10                  15
```

-continued

```
Gln Leu Tyr Lys Thr Cys Lys Gln Ala Gly Thr Cys Pro Pro Asp Ile
             20                  25                  30
Ile Pro Lys Val Glu Gly Lys Thr Ile Ala Glu Gln Ile Leu Gln Tyr
         35                  40                  45
Gly Thr Met Gly Val Phe Phe Gly Gly Leu Gly Ile Gly Thr Gly Ser
     50                  55                  60
Gly Thr Gly Gly Arg Thr Gly Tyr Ile Pro Leu Gly Thr Arg Pro Pro
 65                  70                  75                  80
Thr Ala Thr Asp Thr Leu Ala Pro Val Arg Pro Pro Leu Thr Val Asp
                 85                  90                  95
Pro Val Gly Pro Ser Asp Pro Ser Ile Val Ser Leu Val Glu Glu Thr
                100                 105                 110
Ser Phe Ile Asp Ala Gly Ala Pro Thr Ser Val Pro Ser Ile Pro Pro
            115                 120                 125
Asp Val Ser Gly Phe Ser Ile Thr Thr Ser Thr Asp Thr Thr Pro Ala
        130                 135                 140
Ile Leu Asp Ile Asn Asn Thr Val Thr Thr Val Thr Thr His Asn Asn
145                 150                 155                 160
Pro Thr Phe Thr Asp Pro Ser Val Leu Gln Pro Pro Thr Pro Ala Glu
                165                 170                 175
Thr Gly Gly His Phe Thr Leu Ser Ser Ser Thr Ile Ser Thr His Asn
            180                 185                 190
Tyr Glu Glu Ile Pro Met Asp Thr Phe Ile Val Ser Thr Asn Pro Asn
        195                 200                 205
Thr Val Thr Ser Ser Thr Pro Ile Pro Gly Ser Arg Pro Val Ala Arg
    210                 215                 220
Leu Gly Leu Tyr Ser Arg Thr Thr Gln Gln Val Lys Val Val Asp Pro
225                 230                 235                 240
Ala Phe Val Thr Thr Pro Thr Lys Leu Ile Thr Tyr Asp Asn Pro Ala
                245                 250                 255
Tyr Glu Gly Ile Asp Val Asp Asn Thr Leu Tyr Phe Ser Ser Asn Asp
            260                 265                 270
Asn Ser Ile Asn Ile Ala Pro Asp Pro Asp Phe Leu Asp Ile Val Ala
        275                 280                 285
Leu His Arg Pro Ala Leu Thr Ser Arg Arg Thr Gly Ile Arg Tyr Ser
290                 295                 300
Arg Ile Gly Asn Lys Gln Thr Leu Arg Thr Arg Ser Gly Lys Ser Ile
305                 310                 315                 320
Gly Ala Lys Val His Tyr Tyr Asp Leu Ser Thr Ile Asp Pro Ala
                325                 330                 335
Glu Glu Ile Glu Leu Gln Thr Ile Thr Pro Ser Thr Tyr Thr Thr Thr
            340                 345                 350
Ser His Ala Ala Ser Pro Thr Ser Ile Asn Asn Gly Leu Tyr Asp Ile
        355                 360                 365
Tyr Ala Asp Asp Phe Ile Thr Asp Thr Ser Thr Thr Pro Val Pro Ser
    370                 375                 380
Val Pro Ser Thr Ser Leu Ser Gly Tyr Ile Pro Ala Asn Thr Thr Ile
385                 390                 395                 400
Pro Phe Gly Gly Ala Tyr Asn Ile Pro Leu Val Ser Gly Pro Asp Ile
                405                 410                 415
Pro Ile Asn Ile Thr Asp Gln Ala Pro Ser Leu Ile Pro Ile Val Pro
            420                 425                 430
Gly Ser Pro Gln Tyr Thr Ile Ile Ala Asp Ala Gly Asp Phe Tyr Leu
        435                 440                 445
```

```
His Pro Ser Tyr Tyr Met Leu Arg Lys Arg Arg Lys Arg Leu Pro Tyr
    450                 455                 460

Phe Phe Ser Asp Val Ser Leu Ala Ala
465                 470
```

(2) INFORMATION FOR SEQ ID NO:24:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:24:

CAGGAAACAG CTATGAC                                        17

(2) INFORMATION FOR SEQ ID NO:25:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:25:

CGCCCGGGTT AAAAGTCATC TGCATAAATA TCATATAATC C           41

(2) INFORMATION FOR SEQ ID NO:26:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (xi) SEQUENCE DESCRIPTION: SEQ ID NO:26:

CGCCCGGGTT ATGGTACCGG GGTTGTAGAA GTATCTGTAA TAAAG      45

(2) INFORMATION FOR SEQ ID NO:27:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (xi) SEQUENCE DESCRIPTION: SEQ ID NO:27:

CGCCCGGGTT AATAACCTGA TAAAGATGTA GAGGGTACAG ATGG       44

(2) INFORMATION FOR SEQ ID NO:28:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (xi) SEQUENCE DESCRIPTION: SEQ ID NO:28:

CGCCCGGGTT AACCAAAAGG AATTGTTGTA TTTGCAGGAA TATAACC    47

(2) INFORMATION FOR SEQ ID NO:29:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:29:

CGCCCGGGTT AACCTGATAC TAAAGGAATA TTGTATGCAC C                             41

(2) INFORMATION FOR SEQ ID NO:30:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:30:

GCGGATCCAT GCACAAACGT TCTGCAAAAC GC                                      32

(2) INFORMATION FOR SEQ ID NO:31:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:31:

GCGGATCCAT GAAACGTTCT GCAAAACGCA CAAAACG                                 37

(2) INFORMATION FOR SEQ ID NO:32:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:32:

GCGGATCCAT GCGTTCTGCA AAACGCACAA AACGTGC                                 37

(2) INFORMATION FOR SEQ ID NO:33:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:33:

GCGGATCCAT GTCTGCAAAA CGCACAAAAC GTGCATCGG                               39

(2) INFORMATION FOR SEQ ID NO:34:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:34:

GCGGATCCAT GGCAAAACGC ACAAAACGTG CATCGGC                                 37

(2) INFORMATION FOR SEQ ID NO:35:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:35:

GCGGATCCAT GAAACGCACA AAACGTGCAT CGGCTACC								38

(2) INFORMATION FOR SEQ ID NO:36:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:36:

GCGGATCCAT GCGCACAAAA CGTGCATCGG CTACCC								36

(2) INFORMATION FOR SEQ ID NO:37:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:37:

GCGGATCCAT GACAAAACGT GCATCGGCTA CCCAAC								36

(2) INFORMATION FOR SEQ ID NO:38:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (xi) SEQUENCE DESCRIPTION: SEQ ID NO:38:

GCGGATCCAT GAAACGTGCA TCGGCTACCC AACTTTATAA AAC						43

(2) INFORMATION FOR SEQ ID NO:39:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:39:

GCGGATCCAT GCGTGCATCG GCTACCCAAC TTTATAAAAC							40

(2) INFORMATION FOR SEQ ID NO:40:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:40:

GCGGATCCAT GGCATCGGCT ACCCAACTTT ATAAAAC								37

(2) INFORMATION FOR SEQ ID NO:41:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:41:

GCGGATCCAT GTCGGCTACC CAACTTTATA AAACATG                                37

(2) INFORMATION FOR SEQ ID NO:42:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:42:

GCGGATCCAT GGCTACCCAA CTTTATAAAA CATGC                                  35

(2) INFORMATION FOR SEQ ID NO:43:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:43:

GCGGATCCAT GACCCAACTT TATAAAACAT GCAAACAGG                              39

(2) INFORMATION FOR SEQ ID NO:44:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:44:

GCGGATCCAT GACATGCAAA CAGGCAGGTA CATGTCC                                37

(2) INFORMATION FOR SEQ ID NO:45:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:45:

GCGGATCCAT GATTGCTGAA CAAATATTAC AATATGG                                37

(2) INFORMATION FOR SEQ ID NO:46:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:46:

GCGGATCCAT GGGAACAGGG TCGGGTACAG GCGGACG                                37

(2) INFORMATION FOR SEQ ID NO:47:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:47:

GCGGATCCAT GACAGCTACA GATACACTTG CTCCTG                                      36

(2) INFORMATION FOR SEQ ID NO:48:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:48:

GCGGATCCAT GTCTGATCCT TCTATAGTTT CTTTAG                                      36

(2) INFORMATION FOR SEQ ID NO:49:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:49:

GCGGATCCAT GCGACCCAAA CGTTCTGCAA AACG                                        34

(2) INFORMATION FOR SEQ ID NO:50:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:50:

GCGGATCCAT GCGACACCCA CGTTCTGCAA AACG                                        34

(2) INFORMATION FOR SEQ ID NO:51:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (xi) SEQUENCE DESCRIPTION: SEQ ID NO:51:

GCGGATCCAT GAATCACAAT AATTCTGCAA AACGCACAAA ACG                              43

(2) INFORMATION FOR SEQ ID NO:52:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:52:

GCGGATCCAT GCGACACAAA CCTTCTGCAA AACG                                        34

(2) INFORMATION FOR SEQ ID NO:53:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (xi) SEQUENCE DESCRIPTION: SEQ ID NO:53:

```
GCGGATCCAT GCGACACAAA CGTAATGCAA AACGCACAAA ACG                                    43

(2) INFORMATION FOR SEQ ID NO:54:

(i) SEQUENCE CHARACTERISTICS:
         (A) LENGTH: 34 base pairs
         (B) TYPE: nucleic acid
         (C) STRANDEDNESS: single
         (D) TOPOLOGY: linear (xi) SEQUENCE DESCRIPTION: SEQ ID NO:54:

GCGGATCCAT GCGACACAAA CGTCCTGCAA AACG                                              34

(2) INFORMATION FOR SEQ ID NO:55:

(i) SEQUENCE CHARACTERISTICS:
         (A) LENGTH: 37 base pairs
         (B) TYPE: nucleic acid
         (C) STRANDEDNESS: single
         (D) TOPOLOGY: linear (xi) SEQUENCE DESCRIPTION: SEQ ID NO:55:

GCGGATCCAT GCGACACAAA CGTTCTCCAA AACGCAC                                           37

(2) INFORMATION FOR SEQ ID NO:56:

(i) SEQUENCE CHARACTERISTICS:
         (A) LENGTH: 43 base pairs
         (B) TYPE: nucleic acid
         (C) STRANDEDNESS: single
         (D) TOPOLOGY: linear (xi) SEQUENCE DESCRIPTION: SEQ ID NO:56:

GCGGATCCAT GCGACACAAA CGTTCTGCAC CACGCACAAA ACG                                    43

(2) INFORMATION FOR SEQ ID NO:57:

(i) SEQUENCE CHARACTERISTICS:
         (A) LENGTH: 43 base pairs
         (B) TYPE: nucleic acid
         (C) STRANDEDNESS: single
         (D) TOPOLOGY: linear (xi) SEQUENCE DESCRIPTION: SEQ ID NO:57:

GCGGATCCAT GCGACACAAA CGTTCTGCAA AACCCACAAA ACG                                    43

(2) INFORMATION FOR SEQ ID NO:58:

(i) SEQUENCE CHARACTERISTICS:
         (A) LENGTH: 46 base pairs
         (B) TYPE: nucleic acid
         (C) STRANDEDNESS: single
         (D) TOPOLOGY: linear (xi) SEQUENCE DESCRIPTION: SEQ ID NO:58:

CGGGATCCAT GCGACACAAA CGTTCTGCAA ATAACACAAA ACGTGC                                 46

(2) INFORMATION FOR SEQ ID NO:59:

(i) SEQUENCE CHARACTERISTICS:
         (A) LENGTH: 44 base pairs
         (B) TYPE: nucleic acid
         (C) STRANDEDNESS: single
         (D) TOPOLOGY: linear (xi) SEQUENCE DESCRIPTION: SEQ ID NO:59:

CGCCCGGGCT AGGCAGCCAA AGAGACATCT GAAAAAAAAT ATGG                                   44
```

MODIFIED PAPILLOMA VIRUS L2 PROTEIN AND VLPS FORMED THEREFROM

This application is a continuation of PCT/AU95/00043 filed Jan. 31, 1995.

FIELD OF INVENTION

This invention relates to a modified papilloma virus L2 protein and VLPs formed therefrom, in particular, antigens and vaccines containing said VLPs that may be effective in treatment of infections caused by such viruses.

PRIOR ART

Papilloma viruses (PV) infect both humans and animals (see for review "Papilloma Virus Infections in Animals" by J. P. Sundberg which is described in Papilloma Viruses and Human Disease, edited by K. Syrjanen, L. Gissmann and L. G. Koss, Springer-Verlag 1987). Human papilloma viruses are a family of small DNA viruses which induce benign hyperproliferative lesions of the cutaneous and mucosal epithelia. Of the 70 different virus types which have been identified, more than 20 are associated with anogenital lesions (de Villiers, 1989. J. Virol. 63 4898–4903).

In particular, HPV16 is associated with pre-malignant and malignant diseases of the genito-urinary tract, and in particular, with carcinoma of the cervix (Durst et al., 1983. P.N.A.S. 80 3812–3815; Gissmann et al., 1984. J. Invest. Dermatol. 83 265–285). The detection of antibodies against HPV16 fusion proteins (Jenison et al., 1990. J. Virol. 65 1208–1218; Köchel et al., 1991. Int. J. Cancer 48 682–688) and synthetic HPV16L1 peptides (Dillner et al., 1990. Int. J. Cancer 45 529–535) in the serum of patients with HPV16 infection confirms that there are B epitopes within the capsid proteins of HPV, though few patients have HPV 16L1-specific antibodies identified by these techniques. There is no system for PV propagation in vitro, and human genital lesions associated with HPV16 infection contain few PV particles and low levels of viral structural proteins. Thus further studies on papilloma viruses have been limited.

PV capsids comprise two virally encoded structural proteins, designated L1 and L2, which are assembled onto a DNA-protein complex (Galloway et al., 1989. Adv. Virus Res. 37 125–171). A single virus capsid is a T=7d icosahedron composed of 72 pentameric capsomeres, each of which contains five molecules of the major capsid protein, L1 (Baker et al., 1991. Biophys. J. 60 1445–1456; Finch et al., 1965. J. Mol. Biol. 13 1–12). The minor capsid protein, L2, is present at approximately 1/10 the abundance of L1 (Doorbar et al., 1987. J. Virol. 61 2793–2799) and has an unknown structural role. L1 protein is directed to the nucleus by a C-terminal nuclear localization signal (Zhou et al., 1991. Virology 185 625–632); virus assembly occurs in the nucleus (Orth et al., 1977. J. Virol. 24 108–120; Pfister et al., 1987. Papilloma viruses: particles, genome organisation and proteins, p. 1–18 In K. Syrjanen, L. Gissmann, and L. G. Koss (ed.), Papilloma viruses and human disease. Springer-Verlag KG, Berlin). Recombinant L1 protein self-assembles into particles resembling virus capsids (Zhou et al., 1993. J. Gen. Virol. 74 763–768), but assembly is enhanced in the presence of L2 protein, which may be required for assembly of infectious virions (Hagensee et al., 1993. J. Virol. 67 315–322; Zhou et al., 1991. Virology 185 251–257).

Recombinant PV L1 protein and the combination of recombinant PV L1 and PV L2 proteins have formed the basis of vaccines for the prevention and treatment of papilloma virus infections and used as antigens for the detection of papilloma virus (International Patent Application Publication No. WO93/02184). The presence of the PV L2 protein increases the immunogenicity of the vaccine (Zhou et al., 1991. Virology 185 251–257).

Subsequent to International Publication No. WO93/02184 and the published research by Zhou and others (Zhou et al., 1991, Virology 185 251–257), other workers have developed expression systems for the expression of human papilloma virus VLPs. International Patent Application Publication No. WO94/20137 is directed to the expression of the L1 protein of human papilloma virus and the production of VLPs in Sf-9 insect cells using a baculovirus expression system.

As well, the formation of capsids following expression of L1 and L2 in mammalian cells and insect cells were disclosed in two research articles (Hagensee et al., 1993, J. Virology 67 315 and Kirnbauer et al., 1992, PNAS 89 12180). Two other International Patent Application Publications, namely WO94/00152 and WO94/05792, were directed to recombinant papilloma virus L1 proteins and their use as vaccines and for diagnostic purposes.

One problem, however, with VLP formation which includes PV L2 protein is the incorporation of DNA into the capsid. The inclusion of DNA in the capsid of papilloma virus VLP is not desirable for the vaccines comprising these VLPs. Indeed, in some countries, there are legislative requirements limiting the amount of DNA allowed in a vaccine shot. The level of 10 picograms of DNA per shot has been typically used as an upper limit. This requirement may be due in part to fears of infection from introducing foreign DNA into a healthy individual. The concern with vaccines comprising native L2 protein is that amounts of DNA exceeding this level may be included.

SUMMARY OF THE INVENTION

Thus it is an object of the present invention to provide a virus-like particle that incorporates a substantially minimal amount of DNA.

A further object is to provide a vaccine which overcomes the aforementioned problem.

The invention, therefore, in one aspect, includes a method for production of one or more papilloma virus-like particles (VLPs) which incorporates a substantially minimal amount of DNA including the steps of:

(1) constructing a recombinant DNA molecule which encodes a papilloma virus L2 protein that binds a substantially minimal amount of DNA; and (2) introducing said recombinant DNA molecule into a suitable host cell so that a papilloma virus L1 protein and said papilloma virus L2 protein is expressed and said VLPs are formed therefrom.

The term "a substantially minimal amount of DNA" covers the situation where essentially no DNA is bound by the PV L2 protein or where there is 10 picograms of DNA or less per vaccine shot or other DNA limit set by legislation.

It will be appreciated that a second aspect of the invention lies in the recombinant DNA molecule which encodes said papilloma virus L2 protein.

Further, another aspect of the invention resides in said papilloma virus L2 protein. The L2 protein is preferably modified so that any one or more of the 1–12 amino acid residues adjacent the N-terminal end of the L2 protein are different compared to the wild type L2 protein.

Most preferably the invention includes within its scope L2 mutant(s) shown hereinafter in FIG. 4.

In another aspect, the present invention resides in the novel papilloma virus VLP formed from the said papilloma virus L1 and L2 proteins. The L2 protein forming the VLP preferably has a minimal number of amino acid modifications The invention, in another aspect, includes a vaccine containing the papilloma virus VLPs with or without a suitable adjuvant.

In relation to step (1), the recombinant DNA molecules are suitably constructed from a source of papilloma virus genome whereby the L2 gene may be amplified by PCR amplification using suitably designed primers. The recombinant DNA molecules are preferably amplified from a suitable plasmid containing the PV genome or part thereof. The preferable genome is HPV16 genome.

Preferably primers include those that change one or more of the bases 1–36 from the 5' end of the L2 gene. Changes are preferably by deletion or substitution. A list of the most preferable primers for amplification are listed below (see FIGS. 6, 7 and 8). The L1 and L2 genes may be transcribed from any mammalian or viral promoter with a mammalian or viral polyadenylation signal. Preferably the L1 and L2 genes are transcribed from any vaccinia virus promoter which may be an early promoter or a late promoter as considered appropriate. A list of such promoters is given in Davidson & Moss, 1989, J. Mol. Biol. 210 749–769 and 1989, J. Mol. Biol. 210 771–784. A suitable promoter from which to initiate transcription of the L2 gene is the vaccinia virus late promoter 4b.

The L1 and L2 genes may be encoded on separate vectors or on the same vector. Suitable vectors include plasmids, cosmids and recombinant viruses. Preferably the recombinant DNA molecules are contained in one or more recombinant viruses which may transfect those cells. Suitable viruses that may be used for this purpose include baculovirus, vaccinia, sindbis virus, SV40, Sendai virus adenovirus, retrovirus and poxviruses. Suitable host cells may include host cells that are compatible with the above viruses and these include insect cells such as *Spodoptera frugiperda*, CHO cells, chicken embryo fibroblasts, BHK cells, human SW13 cells, drosophila, mosquito cells derived from *Aedes albopictus* or monkey epithelial cells. It will also be appreciated that other eukaryote cells may comprise yeast cells or other mammalian cells.

Suitable expression systems include prokaryotic expression systems including *E. coli* and any plasmid or cosmid expression vector or eukaryotic systems including host cells described above in combination with a recombinant virus vector or alternatively, yeast cells and yeast plasmids.

The VLPs may be obtained from the transfected cells by any suitable means of purification. A preferable method of production and purification of papilloma virus-like particles is provided in WO93/02184. The VLPs may be combined with any suitable adjuvant such as ISCOMS, alum, Freunds Incomplete or Complete Adjuvant, Quil A and other saponins or any other adjuvant as described for example in Vanselow, 1987, S. Vet. Bull. 57 881–896.

Reference may now be made to various preferred embodiments of the invention as illustrated. In these preferred embodiments, it should be noted that the specific papilloma viruses, VLPs and specific constructs of DNA recombinant molecules are given by way of example.

EXPERIMENTAL

1. Construction of a Modified Palilloma Virus L2 Protein

Materials and Methods

Plasmid construction: For expression in VV, the open reading frame corresponding to the 474-amino-acid HPV16L2 coding region was amplified by PCR from a plasmid containing the HPV16 genome. The 5' primer introduced a BamHI site upstream from the L2 open reading frame ATG and the 3' primer introduced a SmaI sited beyond the termination codon. The amplified L2 fragment was recovered by elution from an agarose gel, cut with BamHI and SmaI, and ligated into RK19 (Kent, 1988. Ph.D. thesis. University of Cambridge, Cambridge, England), creating RK19/16L2, in which L2 expression is driven by the VV late promoter 4b. The HPV16L2 and 4b promoter were then transferred to the VV expression vector pSX3 (Zhou et al., 1991. Virology 185 251–257) for rVV construction.

To create the simplified vector pUC18/4b16L2 and facilitate transfer of mutant L2 genes between vectors used for VV expression, a Klenow-blunted MluI-EcoRI fragment carrying the VV 4b promoter and the whole HPV16L2 open reading frame was cleaved from RK19/16L2 and inserted into pUC18. This plasmid was used as the DNA template for PCR amplifications with primers designed to create C-terminal truncations of L2. Mutants Δ374, Δ384, Δ394, Δ404, and Δ414, C-terminally truncated to residues 374, 384, 394, 404, and 414 of the L2 protein, respectively, were created by using a common 5' primer (M13RSP) (Zhou et al., 1991. Virology 185 625–632) and a panel of 3' primers introducing stop codons (TAA) at codons 374, 384, 394, 404, and 414. To create N-terminal truncation and point mutations, we used a panel of 5' primers. N-terminal deletions (Δ1-2, Δ1-3, Δ1-4, Δ1-5, Δ1-6, Δ1-7, Δ1-8, Δ1-9, Δ1-10, Δ1-11, Δ1-12, Δ1-13, Δ1-14, Δ1-15, Δ1-20, Δ1-40, Δ1-60, Δ1-80, and Δ1-100) were created by using the set of primers which introduced ATG codons at positions corresponding to amino acids 2, 3, 4, 5, 6, 7, 8, 9, 10, 11, 12, 13, 14, 15, 20, 40, 60, 80, and 100, respectively. For N-terminal point mutations (designated H3P; K4P; 2,4,5,N; R5P; S6N; S6P; A7P; K8P; R9P; and 8,9N), amino acids 3, 4, 5, 6, 7, 8, and 9 were changed to either proline (Pro) or asparagine (Asn) by the mismatched-primer method (Zhou et al., 1991. Virology 185 625–632). All mutations were confirmed by direct sequencing of the expression plasmids.

Cells and virus. CV-1 cells were maintained in Dulbecco's modified Eagle's medium (GIBCO) supplemented with 10% fetal or newborn bovine serum (CSL, Melbourne, Australia). Plaque-purified isolates of rVVs were propagated in CV-1 cells grown in Dulbecco's modified Eagle's medium supplemented with 2.5% fetal bovine serum (CSL, Melbourne, Australia).

rVV construction. We used previously described methods (Zhou et al., 1991. Virology 185 251–257) for rVV construction. Briefly, plasmids including the HPV16L2 gene with various mutations driven from the VV late promoter 4b, the *Escherichia coli* gpt gene (Coupar et al., 1988. Gene 68 1–10; Falkner et al., 1988. J. Virol. 62 1849–1854) as a selectable marker, and flanking fragments of the VV B24R gene (Kotwal et al., 1989. J. Virol. 63 600–606; Smith et al., 1989. J. Gen. Virol. 70 233–2343) or thymidine kinase (TK) gene were transfected into VV WR strain-infected (0.05 PFU per cell) CV-1 cells by calcium phosphate precipitation. Virus plaques were purified twice in CV-1 cells in the presence of mycophenolic acid at a concentration of 25 μg/ml.

Immunoprecipitation of L1 and L2 proteins. CV-1 cells were infected with HPV16L1 rVV or HPV16L2 rVV at a multiplicity of infection of about 20 PFU per cell. At 48 h, $5 \times 10^5$ infected cells were lysed with RIPA buffer (150 mM NaCl, 1% Nonidet P-40, 0.5% deoxycholate, 0.1% sodium dodecyl sulfate [SDS], 50 mM Tris [pH 8.0]). Lysed cells were centrifuged briefly at 12,000×g, and the supernatant was used for immunoprecipitation. Immunoprecipitation were carried out with a 1:20 dilution of monoclonal anti-HPV16L1 antibody (McLean et al., 1990. J. Clin. Pathol. 43 488–492) or a 1:2,000 dilution of rabbit anti-HPV16L2 antibody (provided by D. A. Galloway). The precipitated L1 or L2 protein was collected with protein A-Sepharose beads and washed four times in RIPA buffer. Proteins were removed from protein A-Sepharose beads by boiling in polyacrylamide gel electrophoresis (PAGE) sample buffer and separated by SDS-PAGE for analysis.

Southwestern assays. The Southwestern (DNA-protein) assays were based on previously published procedures (McCall et al., 1991. J. Invest. Dermatol. 97 111–114; Moreland et al., 1991. J. Virol. 65 1168–1176). Immunoprecipitated HPV16L1 and HPV16L2 proteins were separated on a SDS-10% polyacrylamide gel and transferred to a nitrocellulose filter by electroblotting. Filters were blocked with blocking buffer (10 mM Tris [pH 7.5], 5% nonfat skim milk, 10% glycerol, 2.5% Nonidet P-40, 0.1 mM dithiothreitol [DTT], 150 mM NaCl) at 4° C. for 12 h. The filters were then washed with binding buffer (10 mM Tris [pH 7.5], 40 mM NaCl, 1 mM EDTA, 1 mM DTT, 8% glycerol, 0.125% skim milk). $^{32}$P-labelled probes were added to binding buffer, and incubation was continued for 4 h at 4° C. The filters were washed with five changes of binding buffer. After being air dried, they were wrapped and exposed to X-ray films. They were subsequently reprobed with anti-HPV16L1 or anti-HPV 16L2 anti-serum and $^{125}$I-protein A to confirm protein transfer.

Binding specificity assay. DNA sequences binding specifically to L2 were selected from a pool of double-stranded, 76-mer oligonucleotides (R76) containing a central stretch of 26 random base pairs, flanked by two unique sequences of 25 bp each (Sorger et al., 1986. J. Mol. Biol. 191 639–658). The sequences of these oligonucleotides were:

R76

5'-CAGGTCAGATCAGCGGATCCTGTCG (N)$_{26}$ (SEQ ID NO:1)

GAGGCGAATTCAGTGCATGTGCAGC-3'(SEQ ID NO:2)

Forward primer 5'-GCTGCACATGCACTGAATTCGCCTC-3'(SEQ ID NO:3)

Back primer 5'-CAGGTCAGATCAGCGGATCCTGTCG-3'(SEQ ID NO:4)

Random oligonucleotide-binding assays were performed essentially as described previously (Treacy et al., 1991. Nature 350 577–584). Briefly, L1 and L2 proteins purified by immunoprecipitation were electrophoresed on an SDS-PAGE gel (10% polyacrylamide) and transferred to a nitrocellulose filter. Filters were incubated for 4 h at 4° C. in buffer A (20 mM N-2-hydroxyethylpiperazine-N'-2-ethanesulfonic acid [HEPES]-HCl [pH 7.9], 1 mM DTT, 10% glycerol, 0.01% Nonidet P-40) containing 50 mM KCl and 5% skim milk. The $^{32}$P-labelled pool of random oligonucleotides was prepared by primed synthesis with the forward primer annealed to the random 76-mer oligonucleotide template, added to the filter, and incubated overnight at 4° C. Washes were performed at 4° C. in buffer A adjusted to 100 mM KCl (two 10-min washes) and then in buffer A adjusted to 200 mM KCl (one 10-min wash). Filters were autoradiographed, the area of the filter corresponding to bound DNA was excised, and the DNA was eluted by heating at 100° C. in water. Eluted DNA was amplified by 30 cycles of PCR with forward and backward primers and purified on 2% agarose gels. For subsequent rounds of binding, the 76-bp product was labelled by 18 cycles of PCR in the presence of $^{32}$P-labelled nucleotide, as described previously (Sorger et al., 1986. J. Mol. Biol. 191 639–658). DNA from the fifth round of selection which remained bound to L2 after washing in buffer A was eluted and amplified as described above, cloned into pUC18, and sequenced.

Immuno-DNA binding assay. Extracts from HPV16L2 rVV-infected cells were prepared and immunoprecipitated as described above. Immune complexes attached to protein A-Sepharose beads were incubated with BamHI-PstI-digested HPV16 DNA for 2 h at 4° C. in DNA-binding buffer (10 mM Tris [pH 7.4], 100 mM NaCl, 1 mM MgCl$_2$, 1 mM EDTA, 8% glycerol, 1 mM DTT, 5% skim milk). Following incubation, the beads were washed five times with the same buffer at room temperature. Protein-DNA complexes were eluted in 1% SDS-5 mM EDTA at 65° C. DNA was extracted with phenol twice and precipitated with ethanol. Samples were run on a 1.5% agarose gel and blotted onto nylon membranes. The DNA bound to the membranes were detected by Southern blotting with $^{32}$P-labelled HPV16 DNA digested with PstI-BamHI.

DNA sequencing. Dideoxy DNA sequencing was performed with the Sequenase version 2.0 kit (U.S. Biochemicals, Cleveland, Ohio). To denature double-stranded DNA for sequencing, we incubated 2 $\mu$g of DNA for 30 min at 37° C. in 200 mM sodium hydroxide. DNA was ethanol precipitated and sequencing carried out as specified by the manufacturer.

Results

Figure 1B:
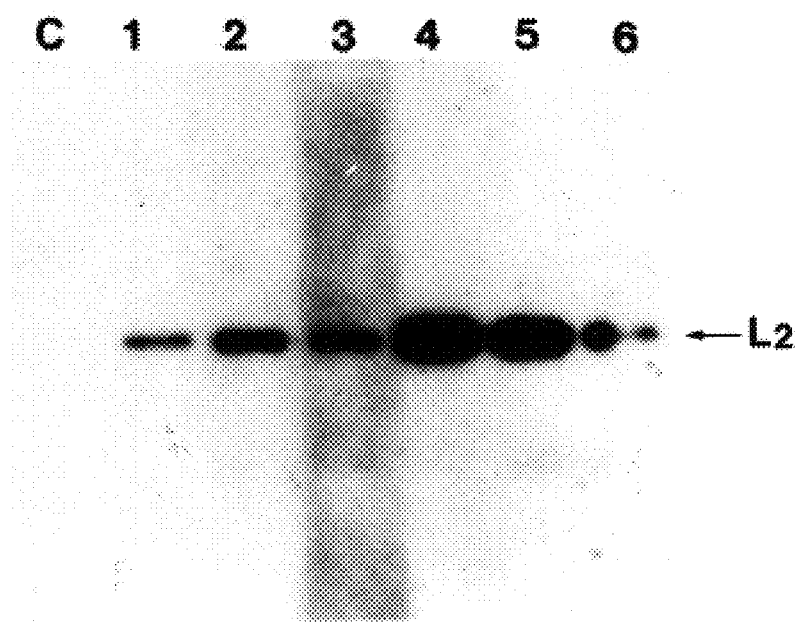

HPV16L2 protein binds DNA. To investigate the DNA-binding activity of PV structural proteins, we expressed HPV16L1 or HPV16L2 in eukaryotic cells by using rVV. L1 and L2 proteins were purified from cell lysates by immunoprecipitation, separated by SDS-PAGE (10% polyacrylamide), and transferred to nitrocellulose filters. Binding of these proteins to DNA was investigated by Southwestern blotting with $^{32}$P-labelled PV genomic DNA and bacteriophage λ DNA in a buffer containing 40 mM NaCl. HPV16L2 protein bound both HPV genomic DNA and λ DNA (FIG. 1B, lanes 2 to 5). HPV16L1 protein, in contrast, failed to bind any labelled DNA (FIG. 1A, lanes 2 to 5), although the purified L1 protein was detectable on the filters by using an anti-HPV16L1 monoclonal antibody (FIG. 1A lanes 1 and 6). Further experiments in buffers containing up to 150 mM NaCl showed no binding of DNA to HPV16L1 (data not shown). These results suggest that HPV16L2 protein, but not HPV16L1 protein, contains DNA-binding sequences and that the recognition of DNA by HPV16L2 may not be sequence specific.

HPV16L2 N terminus is important for DNA binding. To identify the protein sequence responsible for binding of L2 to DNA, we first checked for DNA-binding motifs in the predicted amino acid sequence of HPV16L2. HPV16L2 has two highly charged regions, rich in lysine and arginine. The first makes up the N terminus of the protein (MRHKRSAKRTKR) from amino acids 1 to 12 SEQ ID NO:23; the second lies within the C terminus (RKRRKR) from amino acids 456 to 461 SEQ ID NO:23.

To determine whether either charged region was involved in DNA binding to L2, we made a series of deletion mutants with mutations in HPV16L2. Constructs encoding various C-terminal or N-terminal mutations of HPV16L2 protein were inserted into plasmid pSX3, which had been previously shown to efficiently direct the synthesis of the HPV16L1 proteins in rVVs (Zhou et al., 1991. Virology 185 625–632). CV-1 cells were infected with rVV containing each mutant L2 gene, and cell lysate was analyzed by immunoprecipitation with a rabbit anti-HPV16L2 antibody. The expected relative size of each mutated protein was confirmed by comparing the electrophoretic mobility of truncated proteins with wild-type L2 protein (data not shown).

Figures 2A, 2B:
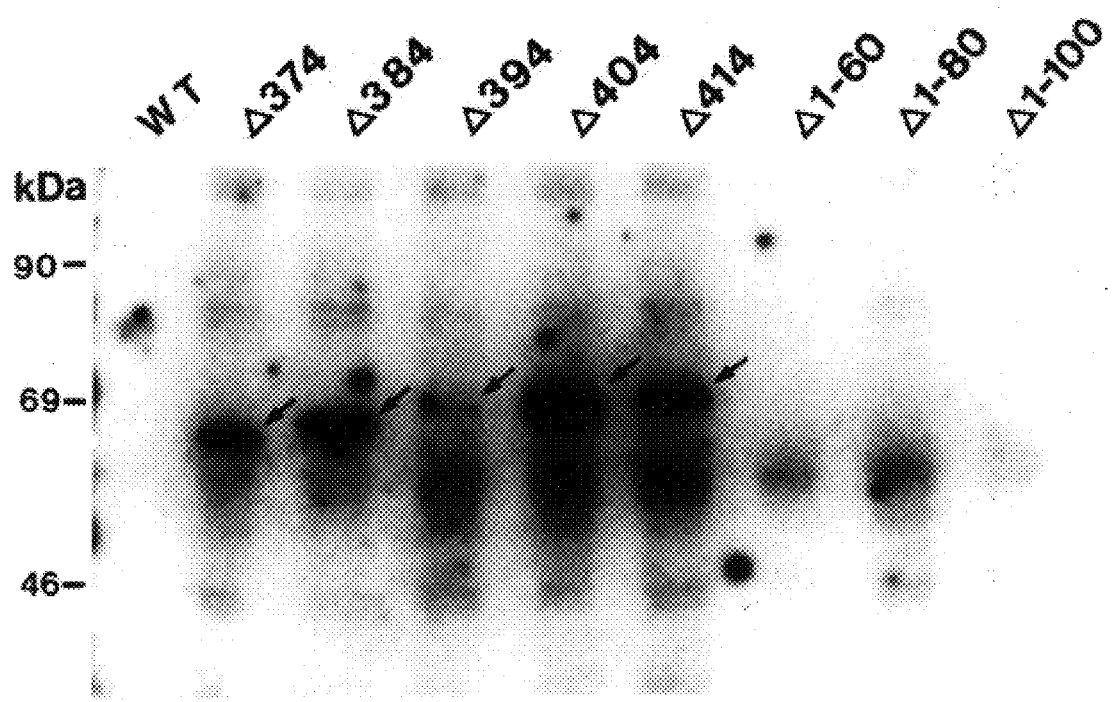
Figure 3A:
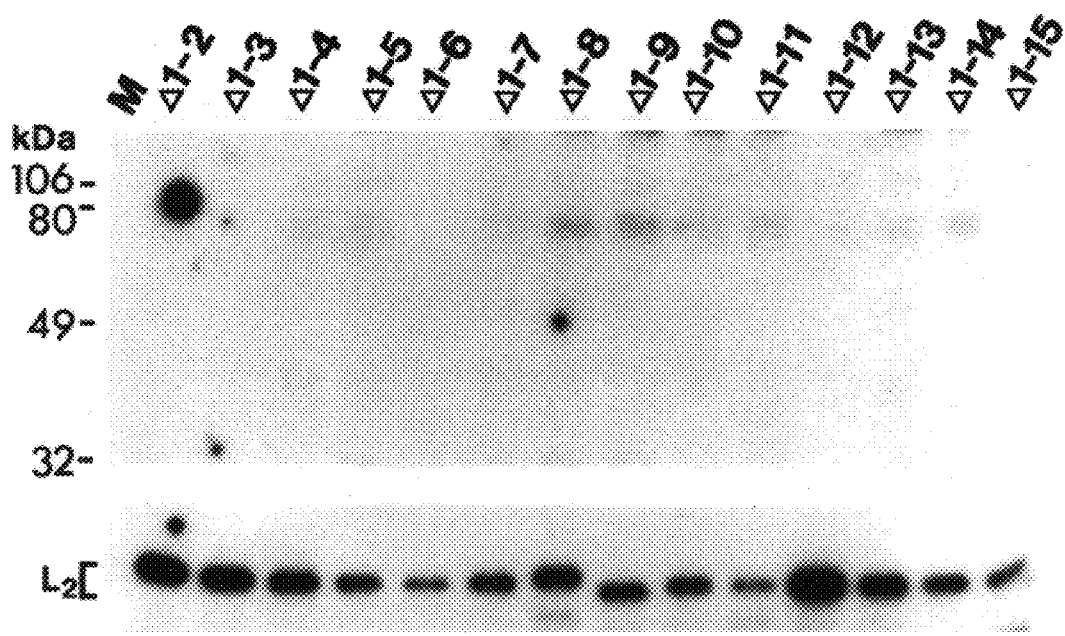

The deletion mutants were examined for binding to $^{32}$P-labelled HPV16 genomic DNA by the Southwestern procedure under conditions associated with binding of native L2 protein. All C-terminal deletion mutants tested, including Δ374, which had the longest deletion, bound HPV DNA in proportion to the amount of immunoreactive L2 protein present (FIG. 2A, lane Δ374). To delineate the contribution of the N terminus of L2 to DNA binding, we constructed N-terminal deletion mutants of L2. Three mutants, in which the first 60, 80 and 100 amino acids of L2 were deleted, each failed to bind HPV DNA (FIG. 2A, lanes Δ1-60 through Δ1-100). To further characterize the N-terminal DNA-binding region, we tested a series of smaller deletions between amino acids 1 and 15 for their DNA-binding activity. Each of these, including the smallest deletion (which was missing only the arginine residue at position 2), failed to bind DNA (FIG. 3A, lanes Δ1-2 to Δ1-15). These results suggested that critical DNA-binding sequences were in the N terminus of L2 and that binding was dependent on charged amino acids including the arginine at position 2.

Figure 3B:
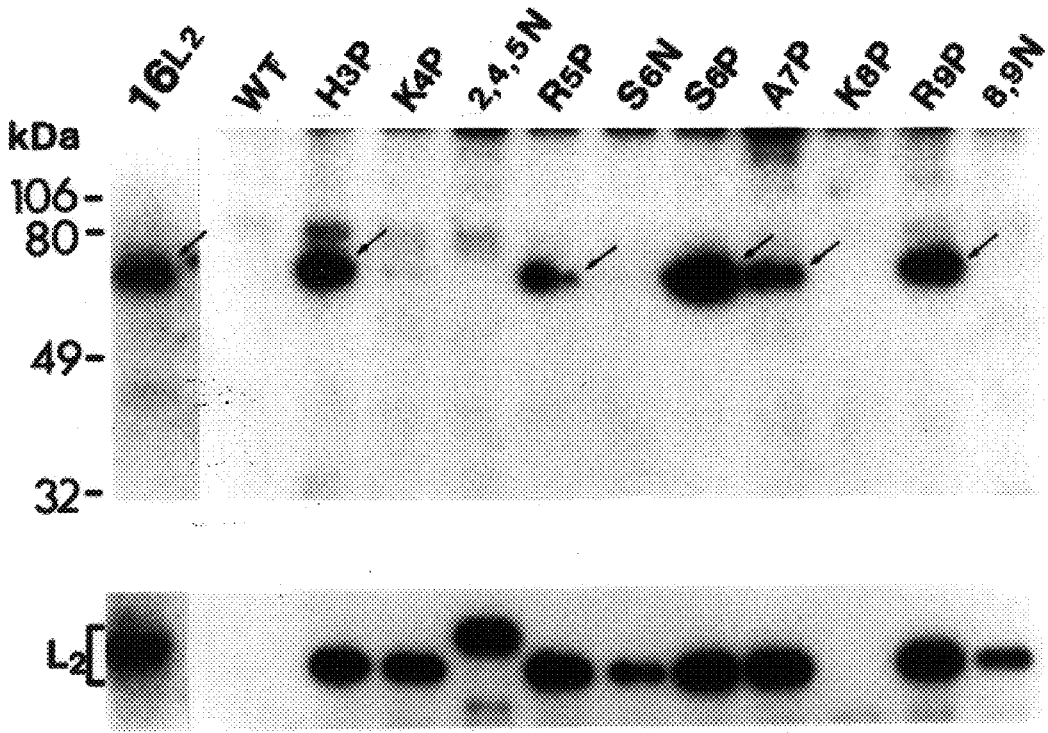

L2 protein uses an arginine-rich motif for DNA binding. The amino acid sequence of the N terminus for HPV16L2, starting from position 1(SEQ ID NO:23), is MRHKRSAKRTKR (one-letter code with charged amino acids underlined). The role of the N terminus of L2 protein in DNA binding was further assessed by site-specific mutagenesis. Ten substitution mutants with mutations of the first 9 amino acids were expressed by rVV, and their DNA-binding activities were examined by Southwestern blotting with $^{32}$P-labelled HPV16 genomic DNA. Similar amounts of the various mutant L2 proteins constructed were available for DNA binding, as determined by analysis of immunoreactive L2 protein on the blots, with the exception of K8P (FIG. 3B, lower panel). Mutation of some charged amino acid residues (Lys-4, Lys-8, Arg-9 ) to Pro or Asn (K4P and 8,9N) abolished DNA binding (FIG. 3B, lanes K4P and 8,9N), while substitution of Arg-5 with Pro (R5P) reduced binding activity (lane R5P). In contrast, substitution of Arg-9 with Pro (R9P) had no effect on DNA binding (lane R9P). Mutation of the neutral amino acids between the Lys-Arg clusters had less effect on DNA-binding activity. Mutations termed H3P, S6P, and A7P, in which substitution of His-3, Ser-6, and Ala-7 for Pro had been produced, showed binding of DNA comparable to that with wild-type L2 (lanes H3P, S6P, and A7P); in contrast, changing Ser-6 to Asn (S6N) abolished DNA binding (lane S6N). These results suggest that the four charged amino acid clusters are important for DNA binding. In each of these charged amino acid clusters, retention of at least one charged amino acid appears necessary for DNA binding. A flexible secondary structure might also be important for L2-DNA interaction because substitution of Ser-6 with Pro and of Arg-5 and Arg-9 did not abolish the DNA binding, whereas the substitution of Ser-6 with Asn removed the L2 DNA-binding function. A summary of L2-DNA interaction results is given in FIG. 4.

Figure 5A:
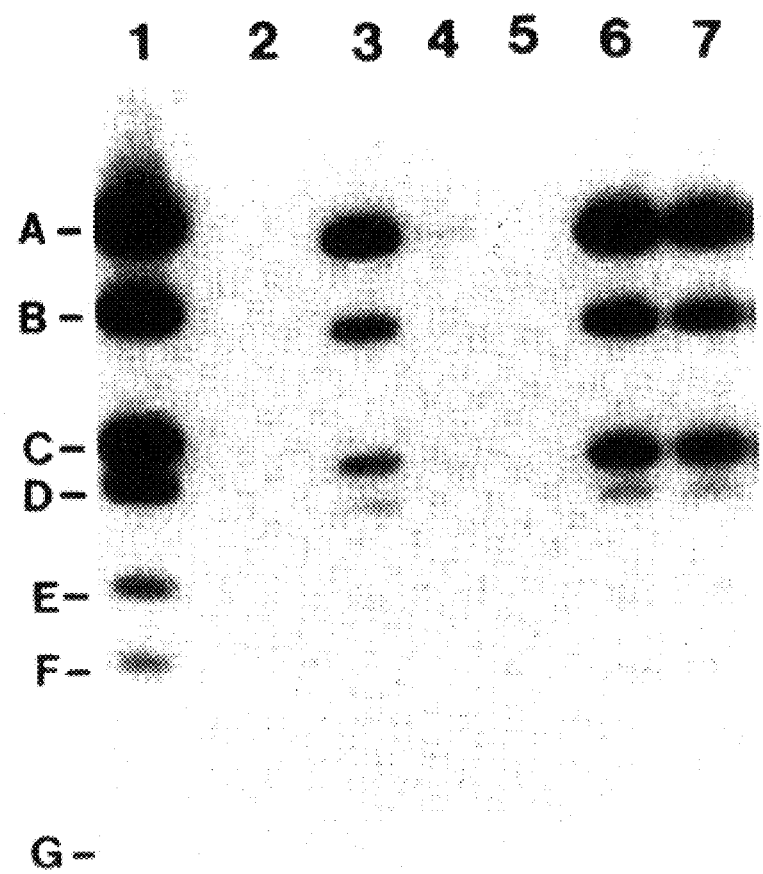
Figure 5B:
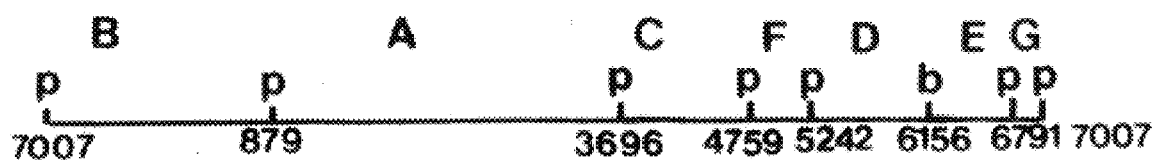

L2-DNA interaction has no DNA sequence specificity. We used a library of oligonucleotides and bound these to purified HPV16L2 protein to select for any high-affinity target DNA sequences. The oligonucleotides were random at 26 positions and were flanked by primer and cloning sequences. After incubation of L2 with a pool of these oligonucleotides, oligonucleotides bound to L2 protein were eluted and amplified by PCR for subsequent rounds of selection. Selection and amplification were carried out six times. DNA clones recovered after the selection rounds 5 and 6 were sequenced. Probability theory predicts that among 52 random 26-mer sequences, any trinucleotide would be found in 20 clones (95% confidence interval, 15 to 26) and any specified sequence of 4 nucleotides would be found in 5 of the 26-mers (95% confidence interval, 0 to 9). Among 52 26-mer clones were observed that the most commonly observed trinucleotide (GGG) was present in 24 clones (twice in 5, three times in 1), whereas the most common series of 4 bp (GGGG) was observed in 8 clones. Thus there was no evidence that any short nucleotide sequence was represented among these clones more frequently than would be expected by chance alone. Further, no more complex conserved nucleotide patterns were observed by using standard sequence alignment programs. These results suggested that high-affinity binding between L2 and DNA is a DNA sequence-independent process. Two additional experiments confirmed this observation. First, extract from cells infected with HPV16L2 rVV was immunoprecipitated with anti-L2 antibody, and the precipitated protein-antibody complexes, attached to Sepharose beads, were allowed to bind to a mixture of restriction fragments from HPV16 genomic DNA. After unbound DNA was washed away, bound DNA fragments were resolved on an agarose gel and detected by Southern blotting with $^{32}$P-labelled HPV16 DNA. An HPV16L2-containing extract, bound to Sepharose beads with anti-L2 antibody, retained each of the HPV16 DNA fragments (FIG. 5A, lanes 3, 6, and 7), whereas none of these fragments were bound by an L1 rVV-infected cell extract bound to the bead with anti-L1 antibody (data not shown) or by wild-type VV-infected cell extract bound to the beads with L2-specific antibodies (FIG. 5A, lane 2). Second, a fixed amount of L2 protein was incubated with $^{32}$P-labelled HPV DNA fragments, in the presence of a 100-fold (lane 4) or 1,000-fold (lane 5) excess of unlabelled λ DNA, and L2, together with any bound DNA, was immunoprecipitated from the mixture by antibody to L2. Phage λ DNA was able to prevent binding of HPV DNA. We conclude that L2 does not interact with DNA in a DNA sequence-specific manner by each of these criteria.

2. Production of Virus-Like Particles with Modified Papilloma Virus L2 Protein

Virus-like particles formed with the modified papilloma virus L2 protein can be produced by the procedures outlined in WO93/02184. A suitable method for the production of virus-like particles is given below by way of example.

CV-1 cells were grown under standard cell culture conditions at 37° C. in an atmosphere of 5% $CO_2$ to a 80% confluency in Dulbecco's modified Eagle's medium (Gibco or CSL) supplemented with 10% foetal calf serum (CSL) in a tissue culture flask. Cells were then infected with 1 to 2 pfu/cell of recombinant vaccinia virus 16L1 (pSX16L$_1$) and recombinant vaccinia virus 16L$_2$ Δ7 (Rkgpt19 Δ1-7) in Dulbecco's modified Eagle's medium supplemented with 2.5% foetal calf serum. Mycophenolic acid was added to the medium at a final concentration of 25 μg/ml. The cell culture was incubated for a further 48–60 hours. Cells were then scraped from the tissue culture flask and pelleted by centrifugation 1,500×g at 4° C. for 10 mins. The pellet was dissolved and the cells were resuspended in 20 ml of phosphate buffered saline (pH 7.4) containing 2 mM PMSF (protease inhibitor). The cell suspension was stored at 4° C. or frozen at −20° C. when the purification procedure was interrupted.

The cell suspension was then placed in a Wheaton glass Dounce homogeniser and kept on ice for 10 mins. Cells were disrupted by 50 strokes of the Dounce homogeniser. A small sample of the resuspension was checked by microscopy to determine whether the cells were disrupted. Homogenization was continued until all the cells were disrupted.

The lysate was centrifuged at 1500×g for 10 mins at 4° C. The cloudy supernatant was discarded and the pellet was resuspended by aspiration in 20 ml of phosphate buffered saline (pH 7.4) containing 2 mM PMSF. The resuspended material was then sonicated (Vibra Cell Sonicator from Sonics Materials Inc. U.S.A., setting 80) for 30 sec on ice in order to release viral particles from the nuclei. The sonicate was diluted to 60 ml with phosphate buffered (pH 7.4) saline containing 2 mM PMSF.

In each of four 38 ml ultra clear centrifuge tubes, 15 ml of resuspended ice cold sonicate was layered on top of 23 ml of ice cold 20% w/v sucrose in phosphate buffered saline (pH 7.4). The sonicate was centrifuged at 95000×g (rotor midpoint) for 2 hrs at 4° C. in a SW-28 rotor. The supernatant and sucrose were discarded and the pellet was washed with phosphate buffered saline (pH 7.4). The pellet was resuspended in 10 ml of phosphate buffered saline (pH 7.4) containing 2 mM PMSF by sonication (Vibra Cell Sonicator from Sonics Materials Inc U.S.A., setting 80) for 60 sec on ice. The resuspension was diluted to 20 ml with phosphate buffered saline (pH 7.4) containing 2 mM PMSF. Cesium chloride was added at 0.481 g/ml to a final volume of 23 ml. The resuspension was centrifuged at 220000×g (mid-tube) for 18 hours at 21° C. in a SW-41 rotor. After centrifugation, two bands were observed. An upper band was observed approximately 1 cm below the meniscus whereas a lower band was noted approximately 1 cm below the upper band. Both bands contained virus-like particles. Both bands were removed by aspiration. The virus-like particles in the upper band were often not as well formed as the virus-like particles from the lower band. The bands were dialysed against 5 liters of phosphate buffered saline (pH 7.4) for 2 hrs at room temperature or up to 24 hrs at 4° C. The virus-like particle preparations were stored at −20° C.

(a) Detection of L1 and L2 Proteins

Samples of cesium chloride purified preparations of virus like particles were diluted (1:10) in 5× reducing buffer (0.05 M (final concentration) Tris-Cl (pH 6.8), 10% glycerol, 10% sodium dodecyl sulphate (SDS), 10% 2-β-mercaptoethanol (0.05%) and made up with water to 100%). The diluted samples were loaded on to SDS-PAGE (10% polyacrylamide) gel and electrophoresed. Standard procedures and conditions were followed (Towbin et al., 1979, Virology 175 1–9).

Molecular weight determination of proteins: Following electrophoresis, the gel was stained for 1–24 hours with coomassie blue stain (coomassie brilliant blue (1 g/l), 40% methanol, 10% acetic acid and 50% water). The gel was destained in methanol-acetic acid solution (40% methanol, 10% acetic acid and 50% water) for 1–24 hours and dried.

Identification of L1 and L2 proteins: On a separate but identical SDS-PAGE gel the protein species contained therein were analysed by western blotting to determine whether the L2 protein was present on the virus like particles. Standard western blotting techniques were employed (Harlow and Lane, 1988, Immunoblotting (Chapter 12) In: Antibody—A laboratory manual, Harlow and Lane (Eds.), Cold Spring Harbour Laboratory Press).

Proteins from the SDS-PAGE gel were transferred to a nitrocellulose filter paper. The nitrocellulose filter paper was cut into strips and blocked with phosphate buffered saline (pH 7.4) containing 5% skim milk powder at 4° C. overnight. The primary antibody was incubated with the nitrocellulose paper strips in phosphate buffered saline (pH 7.4) containing 5% milk powder for 1.5 hours at room temperature with agitation. The primary antibody included monoclonal mouse anti-HPV16L1 antibody and polyclonal rabbit anti-HPV16L1 antibody for the detection of HPV16L1 protein and polyclonal rabbit anti-HPV16L2 antibody for the detection of HPV16L2 protein. Following incubation with the primary antibody the nitrocellulose paper strips were washed three times (10 mins per wash) in phosphate buffered saline (pH 7.4) containing 0.05% tween 20. A second antibody was incubated with the nitrocellulose paper strips in phosphate buffered saline (pH 7.4) containing 5% skim milk powder for 1 hr at room temperature with agitation. The second antibody was either horse radish peroxidase anti-rabbit or horse radish peroxidase anti-mouse immunoglobulin. Three washes as described above were repeated. The nitrocellulose paper strips were rinsed for 30 sec to 1 min with phosphate buffer (pH 7.4). The nitrocellulose paper strips were developed after placing them in a solution containing 18 ml DAB (Di aminobenadine), 27 ml of phosphate buffer (pH 7.6), 3 ml 0.3% cobalt chloride and 30 μl of 30% hydrogen peroxide for 10–90 sec or as soon as the band appears. The nitrocellulose paper strips were rinsed with water and dried.

Total protein determination: Three 5 μl samples from each cesium chloride gradient purified preparation was analysed for the total amount of protein present by BCA protein assay reagent as described by the manufacturer (Pierce).

(b) Detection of Virus-Like Particle Formation

A sample (approximately 0.05 ml) of a virus-like particle preparation that had been purified by centrifugation on a cesium chloride gradient and dialysed against 0.1 M to 0.5 M Tris-HCl for at least 2 hrs but preferably 24 hrs at 4° C. to remove the cesium chloride from the preparation was placed onto a formvar coated EM grid and negatively stained with either 1% or 2% ammonium molybdate (pH 6.5). The grids containing the samples were examine using a Hitachi H-800 transmission electron microscope.

FIGURE LEGENDS

FIG. 1A

Characterization of HPV16L1 DNA-binding activity. HPV16L1 protein, from rVV-infected CV-1 cells, were immunoprecipitated by L1-specific antibodies, separated by SDS-PAGE, and transferred to nitrocellulose. Proteins were renatured in blocking buffer containing DTT and incubated with $^{32}$P-labelled DNA from HPV16 (lane 2), HPV6b (lane 3), HPV11 (lane 4), or phage λ (lane 5). Unbound DNA was removed, and DNA-binding proteins were detected by autoradiography. The position of the L1 protein, determined by immunoblotting, is shown (lanes 1 and 6).

FIG. 1B

Characterization of HPV16L2 DNA-binding activity. HPV161L2 protein, from rVV-infected CV-1 cells, were immunoprecipitated by L2-specific antibodies, separated by SDS-PAGE, and transferred to nitrocellulose. Proteins were renatured in blocking buffer containing DTT and incubated with $^{32}$P-labelled DNA from HPV16 (lane 2), HPV6b (lane 3), HPV11 (lane 4), or phage λ (lane 5). Unbound DNA was removed, and DNA-binding proteins were detected by autoradiography. The position of the L2 protein, determined by immunoblotting, is shown (lanes 1 and 6).

FIG. 2A

Definition of the HPV16L2 DNA-binding region. L2 proteins were separated by SDS-PAGE, transferred to a nitrocellulose filter, and probed with $^{32}$P-labelled HPV16 DNA. C-terminal amino acid deletions are designated as follows: amino acids 374 to 474 as Δ374, 384 to 474 as Δ384, 394 to 474 as Δ394, 404 to 474 as Δ404, and 414 to 474 as Δ414. Removal of amino acids up to 100 from the C-terminal end had no effect on DNA binding. N-terminal amino acid deletions were designated as follows: amino acids 1 to 60 as Δ1-60, 1 to 80 as Δ1-80, and 1 to 100 as Δ1-100. Removal of any N-terminal sequence diminished DNA binding markedly.

FIG. 2B

Definition of the HPV16L2 DNA-binding region. L2 proteins were separated by SDS-PAGE, transferred to a nitrocellulose filter, and probed with L2-specific antiserum. C-terminal amino acid deletions are designated as follows: amino acids 374 to 474 as Δ374, 384 to 474 as Δ384, 394 to 474 as Δ394, 404 to 474 as Δ404, and 414 to 474 as Δ414. N-terminal amino acid deletions were designated as follows: amino acids 1 to 60 as Δ1-60, 1 to 80 as Δ1-80, and 1 to 100 as Δ1-100. The L2 bands are indicated by arrows.

FIG. 3A

HPV DNA L2 protein interactions defined by using mutants with L2 N-terminal mutations. N terminus-truncated L2 proteins, with deletions indicated above each lane, were separated by SDS-PAGE, transferred to nitrocellulose membranes, and incubated with $^{32}$P-labelled HPV16 DNA (upper panel). The $^{32}$P-labelled DNA was removed, and the filter was reprobed with a rabbit anti-HPV16L2 antibody for quantitation of the L2 protein (lower panel). L2 bands are indicated by arrows, and molecular mass markers are indicated on the left. Substitutions are coded as follows: WT, wild-type VV; H3P, His-3 to Pro; K4P, Lys-4 to Pro; 2,4,5N, Arg-2 to Asn, Lys-4 to Asn, Arg-5 to Asn; R5P, Arg-5 to Pro; S6N, Ser-6 to Asn; S6P, Ser-6 to Pro; A7P, Ala-7 to Pro; K8P, Lys-8 to Pro; R9P, Arg-9 to Pro; 8,9N, Lys-8 to Asn, Arg-9 to Asn.

FIG. 3B

HPV DNA L2 protein interactions defined by using mutants with L2 N-terminal mutations. Substitution mutants of L2 proteins, as indicated above each lane, were incubated with $^{32}$P-labelled HPV16 genomic DNA (upper panel) or with rabbit anti-HPV16L2 antiserum (lower panel). L2 bands are indicated by arrows, and the molecular mass markers are shown on the left. Substitutions are coded as follows: WT, wild-type VV; H3P, His-3 to Pro; K4P, Lys-4 to Pro; 2,4,5N, Arg-2 to Asn, Lys-4 to Asn, Arg-5 to Asn; R5P, Arg-5 to Pro; S6N, Ser-6 to Asn; S6P, Ser-6 to Pro; A7P, Ala-7 to Pro; K8P, Lys-8 to Pro; R9P, Arg-9 to Pro; 8,9N, Lys-8 to Asn, Arg-9 to Asn.

FIG. 4

Binding of mutant L2 proteins to HPV DNA. For each mutant, the sequence of the protein is given (single-letter code, with conserved amino acids shown as dashes) and the binding of DNA to the protein by Southwestern blot analysis is indicated by (+ or −(SEQ ID NOS:5–21 are shown in this figure)).

FIG. 5A

DNA-binding assay for HPV16L2 proteins from rVVs. L2 protein was immunoprecipitated with anti-L2 antibody. Equal amounts of L2 protein were incubated with PstI-BamHI-cleaved HPV16 genomic DNA. The bound DNA fragments were eluted with 1% SDS and subjected to Southern blotting with $^{32}$P-labelled HPV16 DNA (lanes 3, 6, and 7). In some experiments, a 100-fold (lane 4) or 1,000-fold (lane 5) molar excess of phage λ DNA was added to the initial incubation of HPV DNA with L2 protein. Mock assay of a control precipitate from wild-type VV-infected cells is also shown (lane 2). On the left the input DNA fragments are labelled from A to G.

FIG. 5B

A linearized map of the HPV16 DNA is shown below. Restriction sites are PstI (p) and BamHI (b), and the corresponding fragments are labelled A to G according to size.

FIG. 6

Amino acid sequence of wild type HPV16L2 protein (SEQ ID NO:23).

FIG. 7

Deoxyribonucleic acid sequence of wild type HPV16L2 gene (SEQ ID NO:22).

FIG. 8

Nucleotide sequence of the PCR primers used to construct HPV16L2 mutants (SEQ ID NOs:24–59).

C-Terminal Deletions

The PCR amplified 4b promoter/L2 fragments were cut with SmaI and cloned into pSX3 (Zhou et al., 1990. J. Gen. Virol. 71 2185–2190) to create vaccinia expression plasmids.

N-Terminal Mutations

The restriction enzyme BamHI and SmaI sites are underlined and start codons ATG and stop codons TAA are in bold. The amplified PCR products were digested with BamHI and SmaI and cloned into the RK19 BamHI/SmaI sites (Kent, 1988). The vaccinia 4b promoter and L2 mutant ORF was cloned into pSX3 (Zhou et al., 1990) to produce vaccinia expressing plasmid containing various L2 mutant ORF.

We claim:

1. A protein consisting of L2 protein which does not bind DNA or which has an impaired ability to bind DNA compared to wild-type papilloma virus L2 protein.

2. A protein comprising a modified papilloma virus L2 amino acid sequence which does not bind DNA or which has an impaired ability to bind DNA compared to wild-type papilloma virus L2 protein, wherein said L2 protein comprises an intact C-terminal region and a modified or deleted N-terminal sequence compared to wild-type papilloma virus L2 protein.

3. The papilloma virus L2 protein of claim 2, wherein said wild-type papillomavirus L2 protein comprises SEQ ID NO:22.

4. The papilloma virus L2 protein of claim 3, wherein one or more of amino acid residues 1 through 15 of SEQ ID NO:22 are modified or deleted.

5. The papilloma virus L2 protein of claim 2, wherein the N-terminal sequence of said L2 protein is selected from the group consisting of SEQ ID NO:6, 7, 8, 10, 11, 13, 16, 18, 19, 20 and 21.

6. The papilloma virus L2 protein of claim 2 which does not bind DNA or which has an impaired ability to bind DNA compared to wild-type papilloma virus L2 protein as detected in a Southwestern blot assay.

7. A nucleotide sequence encoding the papilloma virus L2 protein claimed in claim 2.

8. A vaccine comprising the papilloma virus L2 protein of claim 2 in combination with a suitable adjuvant.

9. A papilloma virus L2 protein which does not bind DNA or which has an impaired ability to bind DNA compared to wild-type papilloma virus L2 protein, wherein said L2 protein is capable of binding papilloma virus L1 protein to form a virus-like particle.

10. The papilloma virus L2 protein of claim 9 having one or more amino acid residues in the N-terminal region that are modified or deleted as compared to wild-type papillomavirus L2 protein.

11. The papilloma virus L2 protein of claim 10, wherein said wild-type papillomavirus L2 protein comprises SEQ ID NO:22.

12. A papillomavirus L2 protein which does not bind DNA or which has an impaired ability to bind DNA compared to wild-type papilloma virus L2 protein, wherein said L2 protein is not a fusion protein.

13. The papilloma virus L2 protein of claim 12 having one or more amino acid residues in the N-terminal region that are modified or deleted as compared to wild-type papilloma virus L2 protein.

14. The papilloma virus L2 protein of claim 11, wherein said wild-type papilloma virus L2 protein comprises SEQ ID NO:22.

15. A method of producing one or more virus-like particles comprising a papilloma virus L1 protein and a papilloma virus L2 protein, wherein said papilloma virus L2 protein does not bind DNA or has an impaired ability to bind DNA compared to wild-type papilloma virus L2 protein, said method comprising the steps of:

(1) constructing a recombinant DNA molecule comprising a DNA sequence encoding said papilloma virus L2 protein wherein said sequence is operably linked to a promoter;

(2) introducing said recombinant DNA molecule into a suitable host cell;

(3) expressing said papilloma virus L2 protein in said host cell in the presence of said papilloma virus L1 protein to form one or more virus-like-particles; and (4) recovering said one or more virus-like-particles from said cell.

16. The method of claim 15, wherein said papilloma virus L2 protein has one or more amino acid residues in the N-terminal region which are modified or deleted compared to wild-type papilloma virus L2 protein.

17. The method of claim 15, wherein said papilloma virus L2 protein is characterized in that one or more of amino acid residues 1 through 15 of SEQ ID NO:22 are modified or deleted.

18. The method of claim 15, wherein the N-terminal sequence of said L2 protein is selected from the group consisting of SEQ ID NO:6, 7, 8, 10, 11, 13, 16, 18, 19, 20 or 21.

19. The method of claim 15, wherein said recombinant DNA molecule also comprises another DNA sequence encoding said papilloma virus L1 protein, wherein said another DNA sequence is operably linked to a promoter.

20. The method of claim 15, wherein said papilloma virus L1 protein is encoded and expressed from a different recombinant DNA molecule than the recombinant DNA molecule encoding the papilloma virus L2 protein.

21. The method of claim 15, further including the step of introducing into said host cell a different recombinant DNA molecule comprising a DNA sequence encoding said papilloma virus L1 protein, wherein said sequence is operably linked to a promoter.

22. Virus-like particles obtainable by the method of claim 15.

23. A vaccine comprising the virus-like particles of claim 22 in combination with a suitable adjuvant.

* * * * *